(12) United States Patent
Bremer et al.

(10) Patent No.: US 11,999,935 B2
(45) Date of Patent: Jun. 4, 2024

(54) BIOREACTOR FOR USE ON A MOVING PLATFORM, BIOREACTOR MOTION SYSTEM, AND METHOD OF PERFORMING A BIOPROCESS USING A BIOREACTOR MOTION SYSTEM

(71) Applicant: Sartorius Stedim Biotech GmbH, Goettingen (DE)

(72) Inventors: Gregory Bremer, Bohemia, NY (US); Clint Kukla, Bohemia, NY (US); Thorsten Adams, Goettingen (DE); Fabian Tunzini, Tagelswangen (CH); Rachel Delessert, Tagelswangen (CH); Michael Bates, Gloucestershire (GB)

(73) Assignee: SARTORIUS STEDIM BIOTECH GMBH (DE)

( * ) Notice: Subject to any disclaimer, the term of this patent is extended or adjusted under 35 U.S.C. 154(b) by 646 days.

(21) Appl. No.: 16/857,296

(22) Filed: Apr. 24, 2020

(65) Prior Publication Data
US 2020/0339931 A1    Oct. 29, 2020

(30) Foreign Application Priority Data
Apr. 24, 2019   (EP) .................................... 19170742

(51) Int. Cl.
*C12M 1/00*   (2006.01)
*C12M 1/36*   (2006.01)
*C12M 3/06*   (2006.01)

(52) U.S. Cl.
CPC ............ *C12M 27/16* (2013.01); *C12M 23/14* (2013.01); *C12M 23/26* (2013.01); *C12M 29/10* (2013.01); *C12M 41/48* (2013.01)

(58) Field of Classification Search
CPC ...... C12M 27/16; C12M 23/14; C12M 23/26; C12M 29/10; C12M 41/48; C12M 33/22; C12M 41/00
See application file for complete search history.

(56) References Cited

U.S. PATENT DOCUMENTS

| 4,910,147 A | * | 3/1990 | Bacehowski | .......... | C12M 23/14 |
| | | | | | 141/10 |
| 9,017,997 B2 | | 4/2015 | Wuenn et al. | | |

(Continued)

FOREIGN PATENT DOCUMENTS

| CN | 102787072 A | * | 11/2012 | ............ | C12M 23/02 |
| EP | 2268788 B1 | | 1/2011 | | |

(Continued)

OTHER PUBLICATIONS

Yang et al., "Journal of Bioscience and Bioengineering, vol. 116 No. 4, 452-459". (Year: 2013).*

(Continued)

*Primary Examiner* — Liban M Hassan
(74) *Attorney, Agent, or Firm* — Dilworth IP, LLC

(57) ABSTRACT

A bioreactor for use on a moving platform including a bag. According to a first aspect, the bag defines a three-dimensional geometrical shape including at least one lower collecting vertex in which at least two edges of the geometrical shape meet at an angle not greater than 90°. The bioreactor further includes at least one port or sensor arranged in the vicinity of the collecting vertex. According to a second aspect, the bag defines a two-dimensional geometrical shape or a three-dimensional geometrical shape. The geometrical shape includes at least one edge, in which at least two faces of the geometrical shape meet at an angle not greater than 90°. A longitudinal port/sensor element is arranged along the edge and includes several ports and/or sensors. A bioreactor (Continued)

motion system including a moving platform and a bioreactor according to the first or second aspect. A method of performing a bioprocess.

19 Claims, 3 Drawing Sheets

(56) References Cited

U.S. PATENT DOCUMENTS

| | | | | |
|---|---|---|---|---|
| 2007/0269888 | A1* | 11/2007 | Houtzager | B01F 31/23 435/235.1 |
| 2009/0291490 | A1* | 11/2009 | Spradling | C12M 23/14 435/292.1 |
| 2010/0203624 | A1* | 8/2010 | Singh | B01F 35/531 435/289.1 |
| 2011/0020922 | A1 | 1/2011 | Wuenn et al. | |
| 2011/0111497 | A1* | 5/2011 | Tamai | C12M 45/09 435/283.1 |
| 2011/0151551 | A1 | 6/2011 | Yi et al. | |
| 2012/0238011 | A1* | 9/2012 | Tuohey | C12M 33/14 435/297.1 |
| 2015/0017716 | A1 | 1/2015 | Kauling et al. | |
| 2015/0160447 | A1* | 6/2015 | Okugawa | G02B 21/244 348/79 |

FOREIGN PATENT DOCUMENTS

| | | |
|---|---|---|
| WO | 2009042432 A1 | 4/2009 |
| WO | 2013124326 A1 | 8/2013 |
| WO | 2017192966 A1 | 11/2017 |
| WO | 2019014541 A2 | 1/2019 |

OTHER PUBLICATIONS

Zhiqiang Han, et al., English Machine translation of CN-102787072-A. Translated on May 25, 2023.*

* cited by examiner

BIOREACTOR FOR USE ON A MOVING PLATFORM, BIOREACTOR MOTION SYSTEM, AND METHOD OF PERFORMING A BIOPROCESS USING A BIOREACTOR MOTION SYSTEM

The invention relates to a bioreactor for use on a moving platform. The invention further relates to a bioreactor motion system comprising a moving platform and a bioreactor. The invention also relates to a method of performing a bioprocess using a bioreactor motion system.

BACKGROUND OF THE INVENTION

Single-use bioreactors comprising bags made from a flexible film material are widely accepted as a tool for cell cultivation. Several technologies exist in the market, including stirred bioreactors, airlift bioreactors, paddle mixed bioreactors, and rocking motion or wave-induced motion systems, which are amongst the most frequently used systems. Rocking platforms for single-use bioreactors were introduced as an alternative to stainless steel agitated-tank bioreactors and offer a lot of advantages. The media surface in the bioreactor is renewed constantly, providing bubble-free aeration with low shear stress acting on the cells. Due to the non-invasive mixing technique there is no risk of contamination or cell damage from impellers.

Current rocking motion bioreactors are flat-shaped, two-dimensional bags made by placing two layers of flexible film material on top of each other and connecting any free edges, e. g. by welding. For cell cultivation, the flat bags are filled with cell culture fluid and placed on a rocking platform that induces waves in the cell culture fluid to provide efficient mixing and gas transfer to respiring cells.

Modern bioprocess monitoring demands sensors that provide on-line information about the process state (temperature, oxygen, pH, etc.). Typical single-use sensors require a port to be welded into a flexible wall of the bioreactor or a dip tube with a sensor at the end of the tube that is submerged in the liquid within the bioreactor. In a rocking motion bioreactor the sensors are usually welded into the bottom wall of the bioreactor.

For some cell cultivations, especially in the context of immunotherapy manufacturing, a relatively low volume range from 50 to 500 mL is required. However, the typical working volumes of common rocking motion bioreactors are greater than 1000 mL. Due to the large bottom dimensions of a common flat bioreactor it cannot be ensured that the sensors at the bottom of the bioreactor are properly covered with the cell culture fluid (biomass), i. e. the liquid may be spread out too thin, if a volume below the specified working volume of the bioreactor is used, e. g. less than 250 mL in a 1000 mL bag.

Typical cell cultivation processes also require to have a filtration membrane installed in the bottom of the bioreactor to remove cell waste while keeping the cells in the bioreactor, a process known as perfusion. In perfusion mode equivalent volumes of media are simultaneously added and removed from the reactor while the cells are retained in the bioreactor. This provides a steady source of fresh nutrients and constant removal of cell waste products. Perfusion is commonly used to attain much higher cell density and thus a higher volumetric productivity than conventional bioreactor batch or fed-batch conditions. For a proper perfusion performance it has to be ensured that the filtration membrane installed in the bottom of the bioreactor is covered by the cell culture liquid when the bioreactor is rocked.

SUMMARY OF THE INVENTION

Accordingly, there is a need for a bioreactor to be used on a moving platform which is suitable for small amounts of liquid, especially in the range of 50 to 500 mL, and guarantees proper sensor monitoring and, if used in perfusion mode, proper filtration performance.

The above problem is solved by a bioreactor according to claim 1 and also by a bioreactor according to claim 2. Advantageous and expedient embodiments of the invention are apparent from the associated dependent claims.

The invention provides a bioreactor for use on a moving platform. While a rocking motion platform is preferred, the term "moving platform" shall also include platforms performing any orbiting, shaking or similar types of movement.

According to a first aspect of the invention, the bioreactor comprises a bag which defines a three-dimensional geometrical shape. The geometrical shape includes at least one lower collecting vertex in which at least two edges of the geometrical shape meet at an angle which is preferably not greater than 90° and more preferably not greater than 60°. The bioreactor further includes at least one port or sensor, e. g. a biomass sensor, a pH sensor, an oxygen saturation ($DO/pO_2$) sensor or any other useful sensor, arranged in the vicinity of the collecting vertex.

According to a second aspect of the invention, while the bag of the bioreactor may define either a two-dimensional or a three-dimensional geometrical shape, the geometrical shape includes at least one edge, in which at least two faces of the geometrical shape meet at an angle which is preferably not greater than 90° and more preferably not greater than 60°. A longitudinal port/sensor element is arranged along the edge and includes several ports and/or sensors.

The invention is based on the finding that a 2D-shaped bag or a 3D-shaped bag can be designed with a special section where even a relatively small amount of liquid, e. g. 50 mL is repeatedly collected (concentrated) when the bag is rocked or otherwise repetitively moved, so that ports and/or sensors arranged in the vicinity of that special section are reliably submerged (covered) by the liquid.

In the sense of the invention, a bag having a three-dimensional geometrical shape according to the first aspect of the invention differs from a conventional two-dimensional bag. It is understood that a two-dimensional bag filled with liquid takes some kind of three-dimensional "cushion" shape, and an empty three-dimensional bag can be pressed into a two-dimensional shape. However, the main difference is that a conventional two-dimensional bag of a bioreactor for use on a moving platform is substantially made from two layers of film material (two separate sheets or one folded sheet) which are connected at their edges, whereas the three-dimensional bag according to the first aspect of the invention has more than two basic wall sections defining a polyhedron shape or another three-dimensional shape having at least one special section that will be explained in detail below.

According to the first aspect of the invention, the special section of the bioreactor bag for collecting the cell cultivation liquid during movement of the bag is the vicinity of a lower (with reference to the use position of the bioreactor on the moving platform) vertex in which at least two edges of the geometrical shape of the bag meet at an angle which is preferably not greater than 90°, more preferably not greater than 60°. This vertex, which is called collecting vertex here for easier distinction from other vertices of the bag shape, can be a corner of a polyhedron, e. g. a tetrahedron, or the tip of a cone (in the latter case two "edges" meeting at the vertex would be any two different lines of the lateral surface of the cone).

It is important to understand that the space in the vicinity of the vertex is confined, especially when one or more of the angles defined by the edges meeting at the collecting vertex is/are acute 90° or even 60°), so that the liquid is concentrated therein and cannot spread away. This effect is used to ensure that the ports and/or sensors arranged in the vicinity of the collecting vertex are sufficiently covered with the cell cultivation liquid to fulfill their functions properly.

The relative term "in the vicinity of the collecting vertex" is used to define a section that is closer to the collecting vertex than to another vertex of the geometrical shape or to an edge not meeting at the collecting vertex.

It is to be noted further that the terms "vertex" and "edge" refer to the geometrical shape defined by the bag of the bioreactor. In practice, a bioreactor bag does not take the perfect geometrical shape of a polyhedron or a cone etc. Accordingly, the before-mentioned terms shall include a vertex or an edge of the bag that is not perfectly sharp but somewhat blunt or round.

According to the second aspect of the invention, the cell cultivation liquid is collected during movement of the bioreactor at an edge of the bag, in which at least two faces of the geometrical shape meet at an angle which is preferably not greater than 90°, more preferably not greater than 60°. Along this edge a longitudinal port/sensor element is arranged which includes several ports and/or sensors. The port/sensor element allows easy installation of a plurality of inlet/outlet lines (hoses or pipes) and/or sensors.

The preferably acute angle of the faces of the bag confines the space in the vicinity of the edge where the faces meet. Accordingly, the cell cultivation liquid is collected there and adequately covers the integrated port/sensor element as desired.

Similar to the explanations further above, a "face" of a bioreactor bag neither has to be perfectly even nor be limited by perfect edges and vertices.

Bioreactors according to the first and second aspects of the invention enable a broad range of working volumes. In particular, the invention makes it possible to use the same bioreactor both for low volumes (50 to 500 mL) and larger volumes (>500 mL) of cell cultivation liquid. This significantly simplifies cell culture processes since multiple processing steps can be performed in the same bioreactor. For example, a small volume batch phase can be followed by a larger volume perfusion phase.

In accordance with the preferred applications of the invention the bioreactor is a single-use bioreactor with a bag made from a flexible film material.

If a port/sensor element is used it can easily be welded between opposite edges of the flexible film material from which the bag is made.

According to a preferred embodiment the port/sensor element is oriented vertically in the use position of the bioreactor. The liquid in the bag will rise up along the port/sensor element when the bioreactor is rocked or otherwise moved in the direction of the port/sensor element.

However, it is also possible that the port/sensor element is oriented horizontally in the use position of the bioreactor.

The plurality of ports of the port/sensor element can be used for various purposes during the cultivation process. In particular, one or more ports of the port/sensor element can be used to connect sensors, e. g. for pH measurement and oxygen saturation ($DO/pO_2$) measurement. The ports can also be used to connect a sample line, input (feed) lines, output (harvest) lines, including inlet and outlet filters, respectively. Moreover, one or more ports can simply be used as an air inlet and/or outlet.

In addition, at least one port can be provided in an upper face of the bag, especially an air outlet.

The bioreactor for use on a moving platform according to the invention can be used in perfusion mode with equivalent volumes of liquid being added and removed at the same time while the cells are retained in the bioreactor. For this purpose, a perfusion membrane is arranged at a bottom face of the bag forming a pocket inside the bag. According to a special, independent aspect of the invention, the bioreactor further comprises a perfusion harvest line or a perfusion harvest port opening through a bottom wall of the bag into the pocket formed by the perfusion membrane. The current state of the art is that a perfusion harvest port is connected to a perfusion membrane on the inside of the bag. A first tube connected to this port extends through the lumen of the bag to a connector with a double hose barb located in the bag film. The line continues on the distal side of the bag with a second tube. In contrast, the invention provides a perfusion harvest line or a perfusion harvest port that is located in the bag film in an area covered by the perfusion membrane on the inside of the bag. The perfusion membrane may be separated from the bag wall by means of a spacer. Thus, the perfusion harvest line extends directly from the underside of the bag. As will be explained later, provision can be made that the line is not pinched between the bottom wall of the bag and the moving platform.

The perfusion membrane can be located in the vicinity of another lower vertex or an edge of the bag remote from the collecting vertex or the port/sensor element. In this case it can be ensured that the perfusion membrane is sufficiently covered with cell cultivation liquid every time the section of the bag including the collecting vertex and/or the port/sensor element is lifted during rocking or a similar movement of the bioreactor.

According to a particularly preferred embodiment of the invention, the bag defines the geometrical shape of a tetrahedron. A tetrahedron is a three-dimensional shape that by definition includes vertices where at least two edges meet at an acute angle. One or more of these vertices can be used as a collecting vertex in the sense of the invention.

However, other three-dimensional geometrical shapes are also possible, like a cone, a frustum or a trough, for example.

As already mentioned, the bioreactor according to the invention is particular valuable as it is possible to use a large bag with both small and large volumes of cell cultivation liquid. Accordingly, in the preferred embodiment of the bioreactor according to the invention the total (geometrical) volume enclosed by the bag equals the total volume of known bioreactors with a designated working volume of at least 1000 mL.

Cell cultures that might be handled in the bioreactor according to the invention include mammalian, insect and plant cells, microbial cultures and shear sensitive cells such as stem cells. Examples comprise cell lines like e. g. from Chinese hamster ovary CHO, VERO cells, human embryonic kidney HEK293. The bioreactor might be used for expansion and differentiation of stem cells, production of recombinant proteins, monoclonal antibodies (mAbs) and vaccines. The bioreactor is especially intended for the culture of any human cells derived from the hematopoetic lineage (blood stem cells, blood progenitor cells, immune cells), like e. g. for gene-modified cell therapies with e. g.

CAR-T, CAR-NK, CD34+HSC, or non-modified cell therapies with e. g. regulatory T (Treg) cells.

The invention also provides a bioreactor motion system according to claim 15. The bioreactor motion system according to the invention comprises a moving platform and a bioreactor according to the first and/or second aspect of the invention. While a rocking motion is preferred, the moving platform may be configured to perform other types of repetitive movements like shaking or orbiting.

If expedient, the moving platform can be equipped with an auxiliary construction including means for altering an effective tilting angle range of a surface on which the bioreactor is to be placed. The auxiliary construction allows the bioreactor to be placed on an existing moving platform in the optimum position and orientation in view of the desired coverage of the ports and/or sensors and the perfusion membrane, if the bioreactor is used in perfusion mode.

In the context of perfusion, the auxiliary construction can also be used to provide a safe passage for a perfusion harvest line so that it can be connected from underneath the bag without being squeezed.

The bioreactor motion system according to the invention may further comprise supporting means, like guiding rails or a recess adapted to the lower shape of the bag, to prevent the bioreactor from shifting or tipping over on the moving platform.

The moving platform is preferably equipped with a load cell in order to automatically determine the weight or the volume of the cell cultivation liquid in the bioreactor.

The invention further provides a method of performing a bioprocess according to claim 20. The method comprises the steps of providing a bioreactor motion system according the invention; filling the bioreactor of the bioreactor motion system with cell cultivation liquid; placing the bioreactor on the moving platform; and moving, especially rocking, the platform repeatedly with a maximum tilting angle which is controlled by a control unit.

Preferably, the control unit (automatically, i. e. without user intervention) adjusts the maximum tilting angle depending on the current volume of the cell cultivation liquid contained in the bioreactor. This is especially useful when a greater tilting angle is required for a low volume of cell cultivation liquid in order to ensure that the ports and/or sensors of the bioreactor are sufficiently covered. With a larger volume of cell cultivation liquid in the bag a smaller tilting angle may be sufficient.

With a load cell provided in the moving platform, the weight of the cell cultivation liquid contained in the bioreactor can be automatically measured, and the volume of the cell cultivation liquid can then easily be calculated from the measured weight.

BRIEF DESCRIPTION OF THE DRAWINGS

Further features and advantages of the invention will become apparent from the following description and from the accompanying drawings to which reference is made. In the drawings.

DETAILED DESCRIPTION OF THE INVENTION

Figure 1:
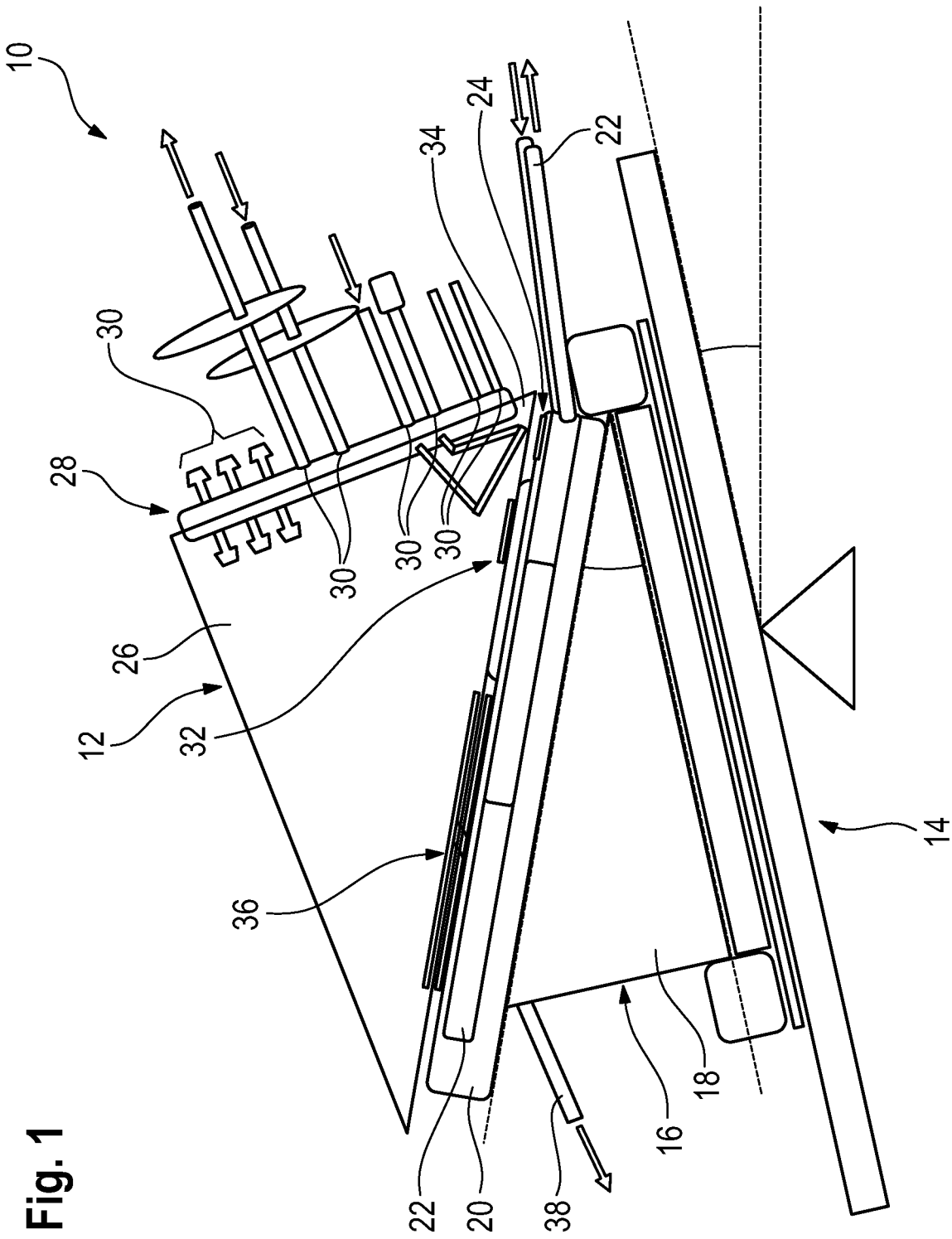
FIG. 1 shows a side view of a bioreactor motion system using a first embodiment of a bioreactor for use on a moving platform according to the invention.

An example set-up of a bioreactor motion system 10 for use in a cell cultivation process is depicted in FIG. 1. The bioreactor motion system 10 includes a single-use bioreactor 12 placed on a moving platform 14 which can be controlled to repeatedly tilt back and forth, or to perform another type of repetitive movement, as is known in the art. According to the side view of FIG. 1, the platform 14 here is tilted clockwise (back) and counter-clockwise (forth).

In the following, it is to be noted that "moving platform" shall include any platform configured to perform an orbiting, shaking or similar types of movement. It is also to be noted that expressions like "back" and "forth" are relative expressions. Depending on the point of view, they could also mean "forth" and "back" or "left" and "right" or "right" and "left" etc., respectively. The terms "upper", "lower", "top", "bottom", "vertical(ly)", "horizontal(ly)" refer to the basic orientation of the bioreactor 12 when placed on the moving platform 14 during the intended use of the bioreactor motion system 10, without being limited in the sense of "perfectly vertical" etc.

In the example set-up the bioreactor 12 is not placed directly on the moving platform 14 but on an auxiliary construction 16. However, for sake of simplicity, the auxiliary construction 16 shall be regarded as part of the moving platform 14. Here, the auxiliary construction 16 includes one or more wedges 18 which are used to alter the effective tilting angle range of the surface on which the bioreactor 12 is placed.

In the present example, the auxiliary construction 16 further includes a generally flat base element 20, and the bioreactor 12 is placed on the upper surface of the base element 20 which is arranged on two spaced-apart wedges 18.

Within the base element 20 a temperature piping 22 is provided, i. e. a piping for circulating a fluid in order to control the temperature of the bioreactor 12 and its content. A temperature sensor 24 arranged between the base element 20 and the bioreactor 12 provides the necessary input for a control unit capable of adjusting the fluid circulation as required.

As already mentioned, the bioreactor 12 is placed on top of the base element 20. If necessary, the bioreactor 12 can be further supported by suitable supporting means, as will be explained later in connection with FIG. 3.

Figure 2:
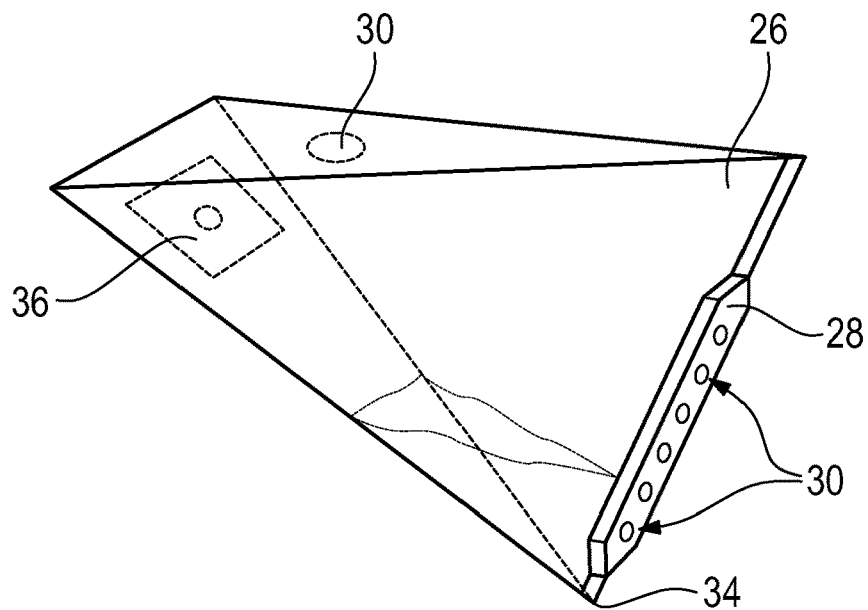
FIG. 2 shows a perspective view of the bag and the port/sensor element used in the bioreactor motion system of FIG. 1.

The bioreactor 12 comprises a closed bag 26 made from a flexible film material. The bag 26 is not a flat, two-dimensional bag but defines a specific three-dimensional geometrical shape. In particular, the bag 26 shown in FIG. 1 has a triangular side face and defines the geometrical shape of a tetrahedron, as can be seen in FIG. 2.

The volume enclosed by the bag 26 is similar to that of a common bioreactor with a designated working volume of 1000 mL or larger.

At a rear end of the bioreactor 12 a longitudinal port/sensor element 28 is arranged along an edge of the bag 26 where two faces of the geometrical shape of the bag meet at an angle which is preferably not greater than 90°, more preferably not greater than 60°. The port/sensor element 28 is made of plastic and is integrated into the wall of the bag 26 by being welded between opposite edges of the film material from which the bag 26 is made. As shown in FIGS. 1 and 2, the edge of the bag 26 where the longitudinal port/sensor element 28 is integrated, is a vertical edge of the tetrahedron-shaped bag 26. The vertical edge extends between bottom and top vertices of the tetrahedron where, respectively, two further edges of the tetrahedron meet.

The port/sensor element 28 includes several ports 30 which are accessible from the outside of the bag 26 and open into the interior of the bag 26. The bag 26 with the integrated port/sensor element 28 is shown separately in FIG. 2.

The ports 30 can be used to connect hoses or pipes, or they can be directly equipped with various sensors. The port/sensor element 28 shown in FIG. 1 provides ports 30 for the following hose/pipe lines and sensors: pH measurement; oxygen saturation (DO/pO$_2$) measurement; sample line; perfusion feed; filter gas inlet; filter gas exhaust. Further ports 30, located at the upper end of the port/sensor element 28, are unused and closed, but may be equipped to provide further functions. It is also possible to provide a biomass sensor at one of the ports 30, or any other useful sensor.

As shown with dashed lines in FIG. 2, one or more ports 30 may be provided in an upper face of the bag 26, e. g. a port used as an air outlet. Correspondingly, one of the upper ports 30 of the port/sensor element 28 can be used as an air inlet.

The bioreactor 12 further includes a biomass sensor 32, e. g. a sensor for measuring a parameter, like capacitance, related to the viable cell density in the cell culture liquid in the bag 26. The biomass sensor 32 is located at the rear end of the bottom of the bag 26 in the vicinity of the port/sensor element 28.

In general terms, the biomass sensor 32, as well as at least the lower ports 30 of the port/sensor element 28, are located in the vicinity of a lower vertex 34 in which at least two (here: three) edges of the geometrical bag shape meet at a preferably acute angle 90° or even 60°). In order to distinguish this vertex 34 from other vertices of the bag shape, it is referenced herein as the "collecting" vertex 34.

A perfusion membrane 36 is also arranged inside the bag 26 at the bottom, but closer to a front end of the bioreactor. The perfusion membrane 36 is separated from the bottom wall of the bag 26 by means of a spacer, thus forming a pocket. A perfusion harvest line 38, or a perfusion harvest port to which a perfusion harvest line can be connected, opens through the bottom wall of the bag 26 into the pocket.

The base element 20 and, if necessary, other components of the auxiliary construction 16, provide a passage to allow a perfusion harvest line 38 to be connected from underneath the bag 26.

During operation of the bioreactor motion system 10, i. e. after the bioreactor 12 has been filled with a volume of 50 to 500 mL and placed (directly or indirectly) on the moving platform 14 and is then repeatedly rocked back and forth, it is ensured that the relevant ports 30 of the port/sensor element 28 as well as the biomass sensor 32 are properly covered with the cell culture liquid when the bioreactor 12 is tilted back (clockwise), and that the perfusion membrane 36 is properly covered with the cell culture fluid liquid the bioreactor 12 is tilted forth (counter-clockwise). This is effected by the tetrahedron shape of the bag 26 and the arrangement of the ports 30 at the rear vertical edge of the tetrahedron, the arrangement of the biomass sensor 32 at the bottom of the tetrahedron close to the collecting vertex 34, and the arrangement of the perfusion membrane 36 at the bottom of the tetrahedron closer to the front end (bottom front edge) of the tetrahedron. In particular, when the bioreactor 12 is tilted back, the cell culture liquid fully or almost fully ascends to the top of the port/sensor element 28 at the rear vertical edge of the bag 26, while the cell culture liquid spreads across and rises above the middle and front portions of the bottom of the bag 26, where the perfusion membrane 34 is located, when the bioreactor 12 is tilted forth. If any air/gas ports or filters are provided at the upper end of the port/sensor element 28, the maximum tilting angle is set such that these ports or filters will not be covered by the cell culture liquid. Similar effects can be achieved with more complex types of movement which include a tilting component, Depending on the volume of cell culture liquid contained in the bioreactor 12, the maximum tilting angle of the moving platform 14 can be varied. While a greater angle is required with a low volume to ensure proper coverage of the ports 30, a smaller angle is sufficient when a large volume of cell culture liquid is in the bag 26 further supporting coverage of the perfusion membrane 34. The maximum tilting angle of the moving platform 14 can be adjusted automatically by a control unit. In order to determine the volume of the cell culture liquid in the bag 26, a load cell connected to the control unit can be used. Such a load cell for measuring weight, from which the volume can be calculated when the density of the cell culture liquid is known, can be a separate or an integrated component of the bioreactor motion system 10.

Figure 3:
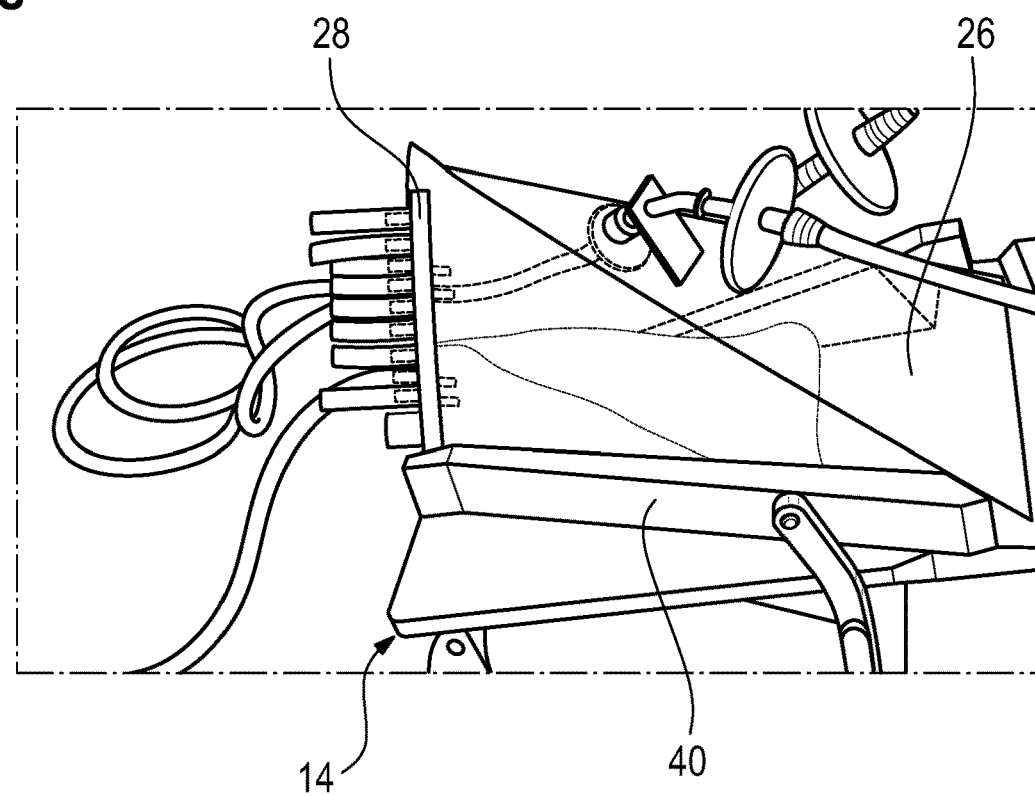
FIG. 3 shows a perspective view of a bioreactor motion system according to the invention with supporting means for the bioreactor.

Depending on the shape of the bag 26, especially of its bottom, it may be useful to provide supporting means 40 to prevent the bioreactor 12 from shifting or tipping over. The supporting means 40 may be guiding rails arranged in accordance with the shape of the lower portion of the bag 26, as shown in FIG. 3, or any other suitable structure for keeping the bioreactor 12 in place.

As explained above, it is preferred, according to a first concept, that the biomass sensor 32 (and/or other sensors) and at least the lower ports 30 of the port/sensor element 28 are located in the vicinity of the collecting vertex 34 where at least two edges of the geometrical bag shape meet at a preferably acute angle, and, according to a second concept, that the port/sensor element 28 is arranged along a rear vertical edge of the bag 26. However, it is also possible to achieve the desired coverage of ports and/or sensors with different designs, other than the one shown in FIGS. 1 to 3, as long as they generally follow one or both of the above concepts.

For example, all relevant sensors and/or ports may be arranged in the area where the biomass sensor 32 is located, not necessarily at the bottom of the bag 26, but possibly also at side faces of the bag 26 in the vicinity of the collecting vertex 34. In this case, the port/sensor element 28 is not mandatory.

Figure 4:
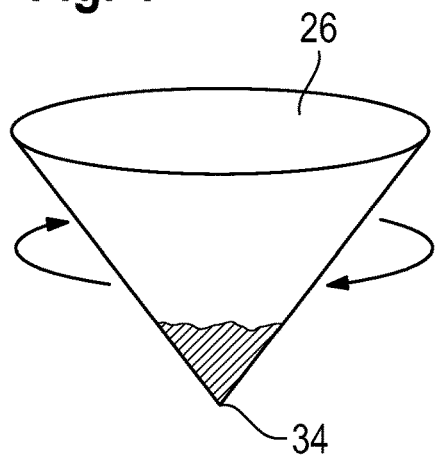
FIG. 4 shows a perspective view of a second embodiment of a bioreactor for use on a moving platform according to the invention.
Figure 5:
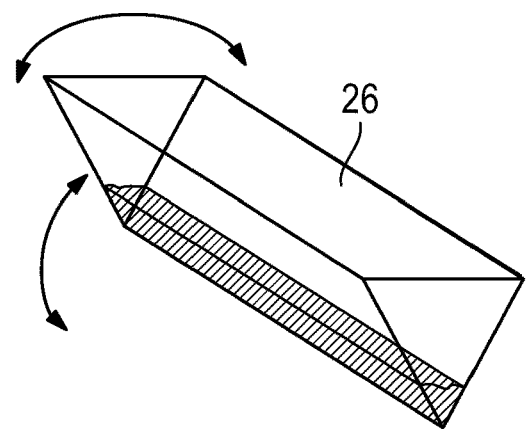
FIG. 5 shows a perspective view of a third embodiment of a bioreactor for use on a moving platform according to the invention.

The bag 26 of the bioreactor 12 may define other suitable three-dimensional geometrical shapes, as shown in FIGS. 4 and 5, for example. In FIG. 4, the bag 26 is generally cone-shaped, arranged such that its collecting vertex 34 is at the bottom. The ports and/or sensors should be arranged in the vicinity of the collecting vertex 34. For this or a similar kind of bag 26 a suitable supporting means 40 is mandatory. The same is true for the trough-shaped bag 26 (triangular prism shape) shown in FIG. 5 having a V-shaped or U-shaped cross section. Depending on the actual movement of the moving platform 14, the sensors and/or ports should be arranged in the vicinity of one of the vertices 34 and/or along the lower edge of the bag 26.

Figure 6:
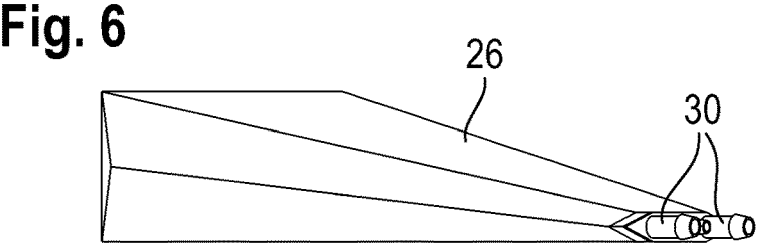
FIG. 6 shows a perspective side view of a fourth embodiment of a bioreactor for use on a moving platform according to the invention.
Figure 7:
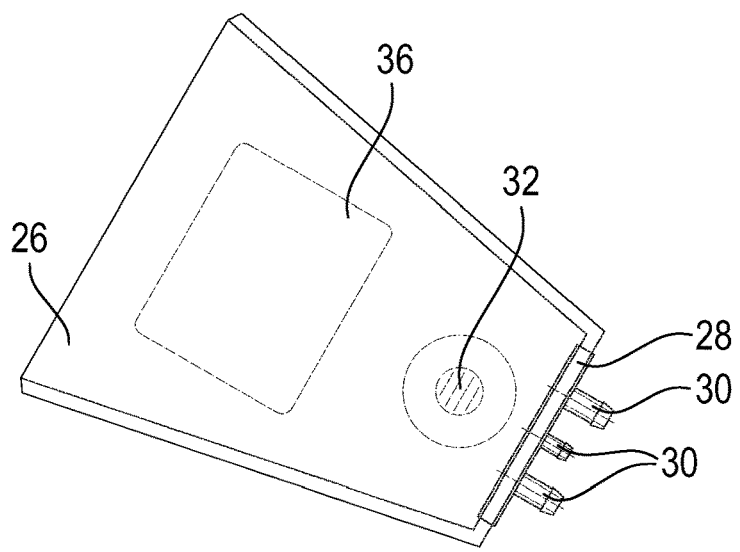
FIG. 7 shows a top view of the fourth embodiment of a bioreactor for use on a moving platform according to the invention.

An embodiment of the bioreactor 12 according to a third concept is shown, by way of example, in FIGS. 6 and 7. The general geometrical shape defined by the bag 26 of the bioreactor 12 is that of a truncated triangular prism. A front end of the bag 26 terminates in a vertically extending quadrilateral face, while the opposite back end of the bag 26 terminates in a horizontal edge into which a longitudinal port/sensor element 28 as described above is incorporated. Bottom and top faces of the geometrical shape defined by the bag 26 meet at this edge in an angle which is preferably not greater than 90°, more preferably not greater than 60°.

Similar to the embodiment shown in FIGS. 1 and 2, a biomass sensor 32 and a perfusion membrane 36 forming a pocket are provided at a bottom face of the bag 26. While the biomass sensor 32 is located in the vicinity of the horizontal edge with the integrated port/sensor element 28, the perfusion membrane 36 is located closer to the vertically extending quadrilateral face at the front end of the bag 26. As described above, the perfusion membrane 36 is separated from the bottom wall of the bag 26 by means of a spacer, and a perfusion harvest line 38 opens through the bottom wall of the bag 26 into the pocket.

In operation of the bioreactor motion system 10 using the bioreactor 12 according to the third concept, the bioreactor 12 is placed such that the swivel axis of the moving platform 14 extends parallel to the horizontal edge where the port/sensor element 28 is integrated. When the bioreactor 12 is tilted back (clockwise according to FIG. 6), the ports 30 of the port/sensor element 28 as well as the biomass sensor 32 are properly covered with the cell culture liquid, while the perfusion membrane 36 is properly covered with the cell culture liquid when the bioreactor 12 is tilted forth (counterclockwise).

In general, if the bag 26 is tilted in a defined back-and-forth manner, then it is preferred—irrespective of the actual three-dimensional geometrical shape defined by the bag 26—that any sensors and/or ports are arranged vertically or, if possible, horizontally along a (virtual) line in one or more walls of the bag 26, the line being perpendicular to the swivel axis of the moving platform 14.

The bioreactor motion system 10 is particularly suitable for cultivation of cells to be used in CAR-T cell therapy, a form of immunotherapy that uses specially altered T cells—a part of the immune system—to fight cancer, but it may also be used for other cell culture applications, such as biopharmaceutical (biologics) production or vaccine production.

LIST OF REFERENCE SIGNS 10 bioreactor motion system
12 bioreactor
14 moving platform
16 auxiliary construction
18 wedges
20 base element
22 temperature piping
24 temperature sensor
26 bag
28 port/sensor element
30 ports
32 biomass sensor
34 collecting vertex
36 perfusion membrane
38 perfusion harvest line
40 supporting means

The invention claimed is:

1. A bioreactor motion system, comprising:
a moving platform;
a bioreactor comprising a bag which defines a three-dimensional geometrical shape including a bottom with respect to a use position on the moving platform and a lower collecting vertex located at the bottom where at least two edges of the three-dimensional geometrical shape meet at an angle, wherein a working volume of the bag is in a range of 50 to 1000 mL; and
a longitudinal port/sensor element arranged along a first one of the at least two edges, the longitudinal port/sensor element including several ports and/or sensors arranged as a single unit,
wherein the longitudinal port/sensor element extends, with respect to its longitudinal direction, along the first one of the at least two edges of the three-dimensional geometrical shape of the bag, the first one of the at least two edges extending from the lower collecting vertex in a direction away from the bottom, such that, when the bioreactor is in the use position on the moving platform, the longitudinal port/sensor element extends away from the moving platform.

2. The bioreactor motion system according to claim 1, characterized in that the angle where the at least two edges of the three-dimensional geometrical shape meet is not greater than 90°.

3. The bioreactor motion system according to claim 1, characterized in that the bioreactor is a single-use bioreactor with the bag being made from a flexible film material.

4. The bioreactor motion system according to claim 3, characterized in that the longitudinal port/sensor element is welded between opposite edges of the flexible film material from which the bag is made.

5. The bioreactor motion system according to claim 1, characterized in that the longitudinal port/sensor element is oriented vertically in the use position of the bioreactor.

6. The bioreactor motion system according to claim 1, characterized in that one or more ports of the longitudinal port/sensor element are used to connect at least one of: a sensor; an input line; an output line; an inlet filter; an outlet filter.

7. The bioreactor motion system according to claim 1, characterized in that at least one other port is provided in an upper face of the bag.

8. The bioreactor motion system according to claim 1, characterized in that a perfusion membrane is arranged at the bottom of the bag, remote from the longitudinal port/sensor element, and forms a pocket inside the bag, the bioreactor further comprising a perfusion harvest line or a perfusion harvest port opening through a bottom wall of the bottom of the bag into the pocket.

9. The bioreactor motion system according to claim 8, characterized in that the perfusion membrane is located in a vicinity of a lower vertex or an edge of the bag remote from the lower collecting vertex or the longitudinal port/sensor element.

10. The bioreactor motion system according to claim 1, characterized in that the bag defines the three-dimensional geometrical shape of a tetrahedron.

11. The bioreactor motion system according to claim 1, wherein the moving platform is a rocking motion platform on which the bottom of the bioreactor is placed adjacent to the moving platform.

12. The bioreactor motion system according to claim 11, characterized in that the moving platform is equipped with an auxiliary construction including means for altering an effective tilting angle range of a surface on which the bioreactor is to be placed.

13. The bioreactor motion system according to claim 11, characterized in that the moving platform is equipped with an auxiliary construction providing a passage to allow a perfusion harvest line to be connected from underneath the bag.

14. The bioreactor motion system according to claim 11, further comprising at least one support to prevent the bioreactor from shifting or tipping over on the moving platform, the at least one support including a rail or a recess.

15. The bioreactor motion system according to claim 11, characterized in that the moving platform is equipped with a load cell.

16. A method of performing a bioprocess, comprising steps of:

providing the bioreactor motion system according to claim 11;
filling the bioreactor with cell cultivation liquid;
placing the bioreactor on the moving platform with the bottom of the bioreactor adjacent to the moving platform; and
moving the moving platform repeatedly with a maximum tilting angle which is controlled by a control unit.

17. The method according to claim 16, characterized in that the control unit adjusts the maximum tilting angle depending on a current volume of the cell cultivation liquid contained in the bioreactor.

18. The method according to claim 17, characterized in that a weight of the cell cultivation liquid contained in the bioreactor is automatically measured, and the current volume of the cell cultivation liquid contained in the bioreactor is calculated from the weight of the cell cultivation liquid.

19. The bioreactor motion system according to claim 1, wherein the longitudinal port/sensor element extends obliquely upwards from the at least one lower collecting vertex but does not reach an opposite vertex at an opposite end of the first one of the at least two edges.

* * * * *